United States Patent
Georis et al.

(10) Patent No.: US 10,986,845 B2
(45) Date of Patent: Apr. 27, 2021

(54) BAKERY PRODUCTS

(71) Applicant: PURATOS NV, Groot-Bijgaarden (BE)

(72) Inventors: Jacques Georis, Couthuin (BE); Valérie Dorgeo, Bertrix (BE); Oksana Shegay, Hasselt (BE); Fanny Nguyen, Bonninne (BE); Bruno Van Winckel, Ghent (BE); Fabienne Verte, Destelbergen (BE); Filip Arnaut, Roosdaal (BE); Thierry Dauvrin, Couthuin (BE)

(73) Assignee: PURATOS NV, Groot-Bijgaarden (BE)

( * ) Notice: Subject to any disclaimer, the term of this patent is extended or adjusted under 35 U.S.C. 154(b) by 40 days.

(21) Appl. No.: 16/091,433

(22) PCT Filed: Apr. 28, 2017

(86) PCT No.: PCT/EP2017/060145
§ 371 (c)(1),
(2) Date: Oct. 4, 2018

(87) PCT Pub. No.: WO2017/186891
PCT Pub. Date: Nov. 2, 2017

(65) Prior Publication Data
US 2019/0142019 A1 May 16, 2019

(30) Foreign Application Priority Data

Apr. 29, 2016 (BE) .................................. 2016/5308
May 18, 2016 (BE) .................................. 2016/5347

(51) Int. Cl.
*A21D 10/00* (2006.01)
*A21D 8/04* (2006.01)
*C12N 9/20* (2006.01)
*C12N 9/18* (2006.01)

(52) U.S. Cl.
CPC ........... *A21D 10/005* (2013.01); *A21D 8/042* (2013.01); *C12N 9/18* (2013.01); *C12N 9/20* (2013.01); *C12Y 301/01004* (2013.01); *C12Y 301/01032* (2013.01)

(58) Field of Classification Search
None
See application file for complete search history.

(56) References Cited

U.S. PATENT DOCUMENTS 6,127,137 A 10/2000 Hasida et al.

FOREIGN PATENT DOCUMENTS

WO 2015/109405 A1 7/2015

OTHER PUBLICATIONS

Whisstock et al. Quaterly Reviews of Biophysics, 2003, "Prediction of protein function from protein sequence and structure", 36(3): 307-340.*
Chica et al., Semi-rational approaches to engineering enzyme activity: combining the benefits of directed evolution and rational design. Curr. Opi. Biotechnol., 2005, vol. 16: 378-384.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Database UniProt, Oct. 19, 2011, Amlacher et al., "Triacylglycerol lipase-like protein, Chaetomium theromphilum", XP002772105, Database accession No. G0SG86_CHATD 100% identical over the full length to SEQ ID No. 1.
Database UniProt, Feb. 17, 2016, Inada et al., "Uncharacterized protein", XP002772106, Database accession No. A0A0S7ALD5_MEIRU 100% identical over the full length to SEQ ID No. 2.
Database UniProt, Aug. 10, 2010, Sikorski et al., XP002772107, Database accession No. D7BCT4_MEISD 100% identical to SEQ ID No. 3.
Gerits et al., 2014, "Lipases and Their Functionality in the Production of Wheat-Based Food Systems", Comprehensive Reviews in Food Science and Food Safety, vol. 13, pp. 978-989.
Jul. 28, 2017, International Search Report and Written Opinion for International Patent Application No. PCT/EP2017/060145, 12 pages.
Oct. 30, 2018, International Preliminary Report on Patentability for International Patent Application No. PCT/EP2017/060145, 8 pages.

* cited by examiner

*Primary Examiner* — Iqbal H Chowdhury
(74) *Attorney, Agent, or Firm* — Lathrop GPM LLP; James H. Velema; Judith L. Stone-Hulslander

(57) ABSTRACT

The present invention relates to compositions and methods for the improvement of bakery products, in particular for the improvement of the texture of cakes and the tolerance of bakery doughs.

5 Claims, No Drawings
Specification includes a Sequence Listing.

BAKERY PRODUCTS

CROSS-REFERENCE TO RELATED APPLICATIONS

This application is a 35 U.S.C. § 371 filing of International Patent Application No. PCT/EP2017/060145, filed Apr. 28, 2017, which claims priority to Belgium Patent Application Nos. 2016/5308, filed Apr. 29, 2016, and 2016/5347, filed May 18, 2016, the entire contents of which are incorporated herein by reference.

FIELD OF THE INVENTION

The present invention relates to novel compositions and methods for the improvement of bakery products, in particular for the improvement of the texture of cakes and the tolerance of bakery doughs.

BACKGROUND OF THE INVENTION

In baking, flour lipids, though representing 2% of flour mass, play an important technological role because they interact with proteins and starch in a dough or a batter, influencing the rheological properties of the dough or the batter, as well as the baked product quality. The lipids can be divided into free lipids and bound lipids, both fractions containing either polar or nonpolar lipids. Approximately, half of the lipids are polar, and the ratio of polar to nonpolar lipids is of great importance in bread making because of its strong correlation with bread volume. The polar lipid fraction is mainly composed of lysophospholipids, phospholipids and galactolipids.

It is important to note that the lipids are located in different places in a dough or a batter. Most of the polar lipids are inside the starch granules. Some free lipids will spontaneously migrate to water gas interfaces, some are on the surface or inside starch granules or attached to gluten molecules and some will only be available after starch gelatinisation.

In general, the major function of lipids is their effect on gas cells stability and gluten strengthening. Also in particular the polar lipids have the ability to reduce starch retrogradation. Gas bubbles stabilization from yeast fermentation leads to larger baked product volume. Strengthening the gluten network leads to a better dough stability and enhances the crumb softness and texture therefore extending the shelf life. However, due to the minor amount of lipids in flour, the native phospholipid fraction of the flour is not enough to give a significant effect by itself on the properties of dough or batter and the quality of baked products. Moreover some of the phospholipid molecules present have no positive effect on dough properties or even a negative effect. Therefore, exogenous phospholipids and/or emulsifiers are used to ensure uniform quality and shelf life stability of baked products. Another way to address this issue is to use lipolytic enzymes (such as phospholipases and lipases) and do an in-situ modification of triglycerides, phospholipids and galactolipids to release the corresponding lysolipids. Lysolipids have better emulsifying properties compared to the original molecules and are more functional as wetting agent in bread and cake making processes.

Furthermore the release of more lysolipids having superior emulsifying properties leads to improved dough or batter rheological properties. Particularly, in cake making, such improved release enhances the air incorporation in the aqueous phase in foam or sponge cake and improves the dispersion of the bakery fat in the batter of layer cakes.

Due to the fact that the lipids are not evenly distributed in dough and batter systems they are not always accessible for hydrolysis by lipases and phospholipases. By changing the pH conditions, the ionic strength and/or the sugar concentration at different temperatures the availability of these lipids will be modified. In such cases one needs enzymes that are active at these different temperatures and conditions and have the desired specificity. On the other hand, hydrolysing the substrates too far will gives rise to molecules with negative effect on baked products quality characteristics.

Although some lipases and/or phospholipases have already been described for their positive properties in the preparation of baked products, the outcome of their use is highly unpredictable, due to their different specificities, their different hydrolysis products, their potential synergies or the process conditions or substrates. Therefore, today, there is still a need for compositions and methods to further improve properties of baked products such as dough or batter tolerance, volume and/or freshness.

SUMMARY OF THE INVENTION

The inventors have found that the use of a particular phospholipase in bakery applications, and in particular in bread making, improves the texture of cakes and the tolerance of bakery doughs.

Accordingly, in a first aspect, the present invention relates to an improver composition comprising a phospholipase having a phospholipase A1 activity/phospholipase A2 activity ratio ranging between 0.01 and 100, preferably ranging between 0.01 and 80, more preferably ranging between 0.01 and 50, more preferably ranging between 0.01 and 10, even more preferably ranging between 1 and 50, even more preferably ranging between 2 and 50, even more preferably ranging between 0.01 and 25, even more preferably ranging between 1 and 25, and even more preferably ranging between 2 and 25, even more preferably ranging between 1 and 10; and having a phospholipase optimum temperature of 45° C. or more. In a particular embodiment the improver composition as disclosed herein provides that for phospholipase A1 activity one milliunit (PA1 mU) is defined as the amount of enzyme that hydrolyses one nanomole (nmol) per minute of fluorescent fatty acid substituted at the sn-1 position of N-((6-(2,4-DNP)Amino)Hexanoyl)-1-(BODIPY® FL C5)-2-Hexyl-Sn-Glycero-3-Phosphoethanolamine at 40° C. and pH 7.4 and for phospholipase A2 activity one milliunit (PA2 mU) is defined as the amount of enzyme that hydrolyses one nanomole (nmole) per minute of fluorescent fatty acid substituted at the sn-2 position of 1-O-(6-BODIPY®558/568-Aminohexyl)-2-BODIPY®FL C5-Sn-Glycero-3-Phosphocholine at 40° C. and pH 8.9 (wherein BODIPY® is generically known as 4,4-difluoro-4-bora-3a,4a-diaza-s-indacene).

In a particular embodiment the improver composition as disclosed herein provides that said phospholipase is chosen from a lipolytic enzyme with phospholipase activity from *Chaetomium thermophilum*, a lipolytic enzyme with phospholipase activity from *Meiothermus ruber* and/or a lipolytic enzyme with phospholipase activity from *Meiothermus silvanus*, preferably a lipolytic enzyme with phospholipase activity from *Meiothermus ruber* and/or a lipolytic enzyme with phospholipase activity from *Meiothermus silvanus*, more preferably a lipolytic enzyme with phospholipase activity from *Meiothermus silvanus*.

In a particular embodiment the improver composition as disclosed herein provides that said phospholipase has a sequence identity of at least 85% with any of SEQ ID NO 1, SEQ ID NO 2 and/or SEQ ID NO 3, preferably of at least 85% with SEQ ID NO 2 and/or SEQ ID NO 3, more preferably of at least 85% with SEQ ID NO 3.

In a particular embodiment the improver composition as disclosed herein provides that said phospholipase retains more than 40% of its phospholipase activity after being incubated for 60 minutes at 50° C., preferably more than 50% of its activity after being incubated for 60 minutes at 50° C.

In a particular embodiment the improver composition as disclosed herein is a bread improver composition or a patisserie mix or premix.

Furthermore, in a further aspect, the present invention relates to the use of a phospholipase in bakery applications, wherein said phospholipase has a phospholipase A1 activity/phospholipase A2 activity ratio ranging between 0.01 and 100, preferably ranging between 0.01 and 80, more preferably ranging between 0.01 and 50, more preferably ranging between 0.01 and 10, even more preferably ranging between 1 and 50, even more preferably ranging between 2 and 50, even more preferably ranging between 0.01 and 25, even more preferably ranging between 1 and 25, and even more preferably ranging between 2 and 25, even more preferably ranging between 1 and 10; and having a phospholipase optimum temperature of 45° C. or more.

In a particular embodiment the use of the composition as disclosed herein is provided wherein said phospholipase has a sequence identity of at least 85% with any of SEQ ID NO 1, SEQ ID NO 2 and/or SEQ ID NO 3, preferably of at least 85% with SEQ ID NO 2 and/or SEQ ID NO 3, more preferably of at least 85% with SEQ ID NO 3.

In a particular embodiment the use of the composition as disclosed herein in bread or patisserie products is provided.

In a particular embodiment the use of the composition as disclosed herein in the preparation of cakes is provided.

Furthermore, in a further aspect, the present invention relates to a method for preparing a baked product, comprising the steps of adding to the dough or batter, prior to baking, a phospholipase having a phospholipase A1 activity/phospholipase A2 activity ratio ranging between 0.01 and 100, preferably ranging between 0.01 and 80, more preferably ranging between 0.01 and 50, more preferably ranging between 0.01 and 10, even more preferably ranging between 1 and 50, even more preferably ranging between 2 and 50, even more preferably ranging between 0.01 and 25, even more preferably ranging between 1 and 25, and even more preferably ranging between 2 and 25, even more preferably ranging between 1 and 10; and having a phospholipase optimum temperature of 45° C. or more.

In a particular embodiment the method as disclosed herein provides that said dough or batter comprises between 5000 and 100000 PmU/100 kg flour, preferably between 7000 and 70000 PmU/100 kg flour, more preferably between 10000 and 60000 PmU/100 kg flour of said phospholipase.

In a particular embodiment the method as disclosed herein provides that said dough or batter shows improved tolerance.

In a particular embodiment the method as disclosed herein provides that said baked product shows improved freshness.

Furthermore, in a further aspect, the present invention relates to a baked product prepared from a dough or batter comprising a phospholipase having a phospholipase A1 activity/phospholipase A2 activity ratio ranging between 0.01 and 100, preferably ranging between 0.01 and 80, more preferably ranging between 0.01 and 50, more preferably ranging between 0.01 and 10, even more preferably ranging between 1 and 50, even more preferably ranging between 2 and 50, even more preferably ranging between 0.01 and 25, even more preferably ranging between 1 and 25, and even more preferably ranging between 2 and 25, even more preferably ranging between 1 and 10; and having a phospholipase optimum temperature of 45° C. or more.

DETAILED DESCRIPTION

Before the present products, compositions, uses and methods of the invention are described, it is to be understood that this invention is not limited to particular products, compositions, uses and methods or combinations described, since such products, compositions, uses and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Disclosed herein are compositions comprising an enzyme having a low phospholipase A1 activity/phospholipase A2 activity ratio; and; having a phospholipase optimum temperature of 45° C. or more which is in particular suitable for use in bakery applications and in particular for use as or in a improver composition.

The inventors have surprisingly found that the use of a particular phospholipase in bakery applications with the particular properties as disclosed herein allows obtaining baked products with improved characteristics. In particular the properties (e.g. tolerance) of the batter and/or dough are improved considerably. Also the baked products have been found to show improved volume and/or freshness.

The compositions as disclosed herein improve particularly (the quality of) bakery products and patisserie products, preferably patisserie products. More particularly, the compositions as disclosed herein improve the tolerance of bakery doughs and the freshness of patisserie products such as cakes, preferably the freshness of cakes.

In the present context the dough tolerance refers to the capacity of a dough or a batter, preferably a bakery dough, to maintain its shape in stress conditions such a prolonged proofing time or mechanical shocks during or after proofing and to provide, after baking, a baked product with properties (e.g. volume) comparable to a baked product obtained with an unstressed dough or batter.

In the present context freshness refers to a combination of texture parameters such as softness, moistness, cohesiveness, gumminess and resiliency. Loss of freshness is usually associated with staling. More particularly an improved freshness of a baked product corresponds to an improved softness and/or an improved moistness and/or an improved short bite when compared to a reference. These parameters may be advantageously measured by physical methods such as with a texturometer or by sensorial analysis conducted with a panel of expert judges.

The softness of a cake refers to the feeling related to the force required to compress and bite the cake crumb. Cake moistness is the moist sensation (opposite of dryness) perceived when touching and eating the cake. Touching a moist cake with the lips and/or the hands gives a colder sensation on lips and/or compared to a dry cake. In the mouth a moist cake is felt as humid and juicy. When eating a moist cake, there is no feeling that it absorbs water from the inside of the mouth. Softness and moistness in cakes are different parameters. For example, traditional sponge cakes are very soft, though they are perceived as not moist (very dry). On the other hand, some brownies can be perceived as very moist and yet be hard and dense. Moisture migration from crumb to crust and amylopectin retrogradation are identified as the main causes of cake firming and cake drying during storage.

As used herein, the term "lipase" refers generally to triacylglycerol lipases or triacylglycerol acylhydrolase as defined by enzyme entry EC 3.1.1.3. Lipases are defined herein as enzymes that catalyse the hydrolysis of triacylglycerols to give free fatty acids, diacylglycerols, monoacylglycerols and glycerol. The lipase used in the compositions defined herein may comprise enzymatic side-activities such as for example phospholipase activity.

In the context of the present invention the lipase activity is measured using p-nitrophenyl palmitate (pNPP) as substrate and according to the method described herein. The enzyme activity can also be measured with other assays for lipase activity known by persons skilled in the art (for a review see for example Stoytcheva M. & al, 2012, Current Analytical Chemistry, vol 8, p. 400).

In particular, the lipase activity is measured using p-nitrophenyl palmitate (pNPP) as substrate. The release of yellow p-nitrophenol due to hydrolysis of p-nitrophenyl palmitate by lipase is measured by spectrophotometry at 414 nm. One lipase milliunit (LmU) is defined as the amount of enzyme needed to release one nanomole (nmole) per minute of p-nitrophenol from p-nitrophenyl palmitate at 40° C. and pH 7.5. More details on the lipase activity measurement are given in the examples.

As used herein, the term "phospholipase" refers generally to enzymes that hydrolyse phospholipids into fatty acids and other lipophilic substances like for example lysophospholipids, diacylglycerols, choline phosphate and phosphatidates, depending on the site of hydrolysis. Depending on the specific bond targeted in the phospholipids molecule, phospholipases are classified in different types such as A, B, C and D.

In the context of the present invention the phospholipase activity is measured using p-nitrophenyl phosphorylcholine as substrate, wherein the phospholipase activity is expressed in milliunits (PmU) that is defined as the amount of enzyme needed to release one nanomole (nmole) of p-nitrophenol from p-nitrophenyl phosphorylcholine per minute at 50° C. and pH 7.5. The phospholipase activity can also be measured with other assays for phospholipase activity known by persons skilled in the art such as the hydrolysis of phosphatidylcholine.

In particular, the phospholipase activity is measured using p-nitrophenyl phosphorylcholine (pNPPC) as substrate. The release of yellow p-nitrophenol due to hydrolysis of p-nitrophenyl phosphorylcholine by phospholipase is measured by spectrophotometry at 414 nm. One phospholipase milliunit (PmU) is defined as the amount of enzyme needed to release 1 nmol of p-nitrophenol per minute at 50° C. and pH7.5. More details on the phospholipase activity measurement are given in the examples.

As used herein, the term "phospholipase A" refers to lipolytic enzymes that catalyse in the hydrolysis of one or more bonds in phospholipids. Two different types of phospholipase A activity can be distinguished which hydrolyse the ester bond(s) that link the fatty acyl moieties to the glycerol backbone. Phospholipase A1, as defined by enzyme entry EC 3.1.1.32, and Phospholipase A2, as defined by enzyme entry EC 3.1.1.4, catalyse the deacylation of one fatty acyl group in the sn-1 and sn-2 positions respectively, from a diacylglycerophospholipid to produce lysophospholipid.

In the context of the present invention the phospholipases activities are measured using respectively a lipid mix of dioleoylphosphatidylcholine, dioleoylphosphatidylglycerol and dye labelled N-((6-(2,4-DNP)Amino)Hexanoyl)-1-(BODIPY®FL C5)-2-Hexyl-Sn-Glycero-3-Phosphoethanolamine (for phospholipase A1) or a lipid mix of dioleoylphosphatidylcholine, dioleoylphosphatidylglycerol and dye labelled 1-O-(6-BODIPY® 558/568-Aminohexyl)-2-BODIPY®FL C5-Sn-Glycero-3-Phosphocholine (for phospholipase A2) as substrates and according to the methods described herein (wherein BODIPY® is generically known as 4,4-difluoro-4-bora-3a,4a-diaza-s-indacene). The phospholipase activities can also be measured with other assays for lipase activity known by persons skilled in the art, such as using rac-1,2-S,O-didecanoyl-3-phosphocholine-1-mercapto-2,3-propanediol substrate for assaying phospholipase A1 activity and 2-hexadecanoylthio-1-ethyl-phosphocholine substrate for assaying phospholipase A2 activity.

In particular, the phospholipase A1 (PLA1) activity is measured using a lipid mix of dioleoylphosphatidylcholine, dioleoylphosphatidylglycerol and dye labelled N-((6-(2,4-DNP)Amino)Hexanoyl)-1-(BODIPY®FL C5)-2-Hexyl-Sn-Glycero-3-Phosphoethanolamine (PED-A1) as substrate (that can be found for example in the EnzChek Phospholipase A1 assay kit-ThermoFisher Scientific, and wherein BODIPY® is generically known as 4,4-difluoro-4-bora-3a,4a-diaza-s-indacene). The PED-A1 is specific for PLA1 and is a dye-labelled glycerophosphoethanolamine with BODIPY®FL dye-labelled acyl chain at the sn-1 position and dinitrophenyl quencher-modified head group (wherein BODIPY® is generically known as 4,4-difluoro-4-bora-3a, 4a-diaza-s-indacene). One phospholipase A1 milliunit (PA1 mU) is defined as the amount of enzyme needed to release one nanomole (nmole) per minute of fluorescent fatty acid substituted at the sn-1 position of PED-A1 at 40° C. and pH7.4. More details on the phospholipase A1 activity measurement are given in the examples.

In particular, the phospholipase A2 (PLA2) activity is measured using a lipid mix of dioleoylphosphatidylcholine, dioleoylphosphatidylglycerol and dye labelled 1-O-(6-BODIPY®558/568-Aminohexyl)-2-BODIPY®-FLC5-Sn-Glycero-3-Phosphocholine) (Red/Green BODIPY®PC-A2) as substrate (that can be found for example in the EnzChek Phospholipase A2 assay kit-ThermoFisher Scientific, and wherein BODIPY® is generically known as 4,4-difluoro-4-bora-3a,4a-diaza-s-indacene). The Red/Green BODIPY®PC-A2 substrate is selective for PLA2 and provides sensitive and continuous rapid real-time monitoring of PLA2 enzyme activities. One phospholipase A2 milliunit (PA2 mU) is defined as the amount of enzyme needed to release one nanomole (nmole) per minute of fluorescent fatty acid substituted at the sn-2 position of Red/Green BODIPY®PC-A2 at 40° C. and pH 8.9 (wherein BODIPY® is generically known as 4,4-difluoro-4-bora-3a,4a-diaza-s-indacene). More details on the phospholipase activity A2 measurement are given in the examples.

Accordingly, in a first aspect, the present invention relates to an improver composition comprising a phospholipase having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and; having a phospholipase optimum temperature of 45° C. or more.

In particular the phospholipase has an optimum temperature equal or higher than 45° C. and retains more than 40%, preferably more than 50% of its activity after 60 minutes at 50° C.

The activity is measured by determining the phospholipase activity as indicated herein (using p-nitrophenyl phosphorylcholine as substrate).

In a particular embodiment the improver composition as disclosed herein provides that for phospholipase A1 activity one milliunit (PA1 mU) is defined as the amount of enzyme that hydrolyses one nanomole (nmol) per minute of fluorescent fatty acid substituted at the sn-1 position of N-((6-(2,4-DNP)Amino)Hexanoyl)-1-(BODIPY®FL C5)-2-Hexyl-Sn-Glycero-3-Phosphoethanolamine at 40° C. and pH 7.4 and for phospholipase A2 activity one milliunit (PA2 mU) is defined as the amount of enzyme that hydrolyses one nanomole (nmole) per minute of fluorescent fatty acid substituted at the sn-2 position of 1-O-(6-BODIPY®558/568-Aminohexyl)-2-BODIPY®FL C5-Sn-Glycero-3-Phosphocholine at 40° C. and pH 8.9 (wherein BODIPY® is generically known as 4,4-difluoro-4-bora-3a,4a-diaza-s-indacene).

In a particular embodiment the improver composition as disclosed herein provides that said phospholipase is chosen from a lipolytic enzyme with phospholipase activity from *Chaetomium thermophilum*, a lipolytic enzyme with phospholipase activity from *Meiothermus ruber* and/or a lipolytic enzyme with phospholipase activity from *Meiothermus silvanus*, preferably a lipolytic enzyme with phospholipase activity from *Meiothermus ruber* and/or a lipolytic enzyme with phospholipase activity from *Meiothermus silvanus*, more preferably a lipolytic enzyme with phospholipase activity from *Meiothermus silvanus*.

In a particular embodiment the improver composition as disclosed herein provides that said phospholipase has a sequence identity of at least 85% with any of SEQ ID NO 1, SEQ ID NO 2 and/or SEQ ID NO 3, preferably of at least 85% with SEQ ID NO 2 and/or SEQ ID NO 3, more preferably of at least 85% with SEQ ID NO 3 (see table A).

More particularly said phospholipase has a sequence identity of at least 85%, preferably at least 90%, more preferably at least 95% to SEQ ID NO 1, SEQ ID NO 2 and/or SEQ ID NO 3, preferably of at least 85%, preferably at least 90%, more preferably at least 95% to SEQ ID NO 2 and/or SEQ ID NO 3, preferably of at least 85%, preferably at least 90%, more preferably at least 95% to SEQ ID NO 3 (see table A).

More particularly said phospholipase has a sequence identity of 100% to SEQ ID NO 1, SEQ ID NO 2 and/or SEQ ID NO 3, preferably of 100% to SEQ ID NO 2 and/or 3, more preferably of 100% to SEQ ID NO 3.

TABLE A

| Name | Sequence |
| --- | --- |
| SEQ ID NO 1 (protein) PH2 [Chaetomium | MKGFLLASLAALAVAAPSSKKQRAAPVTAQQLNNFKLYMQWSSASHCAN EAPIGSVVTCTDNQCSMFQSHNATVAATFIGSILDMRGFLGIDDVDKNIVLS FRGSTSWRNWIADAIFVQTPCDLTPGCLVHAGFYASWLEIKNSVIDAVKAA |

TABLE A-continued

| Name | Sequence |
|---|---|
| *thermophilum*] | KAAHPNYKLVTTGHSLGAAVATLAAATLRKAGPIEILYTYGSPRVGNKAFA<br>EFVTNQAGGEYRLTHSADPIPRLPPIIFNYRHTSPEYWFDEGEDGVVTVDE<br>FQICEGYANVNCNAATSGFNMDLHGWYFQNHQGCSLGYTPWRAVKERE<br>LSDPELEALVNRFAEMDKAYVENLNLEGLEP |
| SEQ ID NO 2<br>(protein) PH3<br>[*Meiothermus ruber*] | MGKPMRFAVGILALLLAACSQPATESTSASIVEDMRQLGVEPEAIAAYTEA<br>LQNLEQARLALQSLGAGDLLLVQSIALGSVANYDAYYNARASYPQFDWSR<br>NGCSAPEGLGLGYRETFRPACNVHDFGYANFPRFPSLYNETGRKLSDDN<br>FLVNMNQICRPRSFLSRSACYSAAYAYYLAVRSAGWAYFYD |
| SEQ ID NO 3<br>(protein) PH4<br>[*Meiothermus silvanus*] | MRVVLLMLVLVLAACGSQTGAPNWTLEQIAALTPEQIDALSEGELQKIQTIL<br>QPEFARVESQLIQLQSQLEALVAAQDSRWPNFDYTVYLATAIPYGTFFTYY<br>RTYSGPDWSNDGCSYSPDKPLFLNFKDPCNHHDFGYR |
| SEQ ID NO 4<br>(DNA) PH2<br>[*Chaetomium thermophilum*] | ATGAAGGGCTTCCTGCTGGCCAGCCTGGCCGCCCTGGCCGTGGCCGC<br>CCCCAGCAGCAAGAAGCAGCGCGCCGCCCCCGTGACCGCCCAGCAG<br>CTGAACAACTTCAAGCTGTACATGCAGTGGAGCAGCGCCAGCCACTGC<br>GCCAACGAGGCCCCCATCGGCAGCGTGGTGACCTGCACCGACAACCA<br>GTGCAGCATGTTCCAGAGCCACAACGCCACCGTGGCCGCCACCTTCA<br>TCGGCAGCATCCTGGACATGCGCGGCTTCCTGGGCATCGACGACGTG<br>GACAAGAACATCGTGCTGAGCTTCCGCGGCAGCACCAGCTGGCGCAA<br>CTGGATCGCCGACGCCATCTTCGTGCAGACCCCCTGCGACCTGACCC<br>CCGGCTGCCTGGTGCACGCCGGCTTCTACGCCAGCTGGCTGGAGATC<br>AAGAACAGCGTGATCGACGCCGTGAAGGCCGCCAAGGCCGCCCACCC<br>CAACTACAAGCTGGTGACCACCGGCCACAGCCTGGGCGCCGCCGTGG<br>CCACCCTGGCCGCCGCCACCCTGCGCAAGGCCGGCATCCCCATCGAG<br>CTGTACACCTACGGCAGCCCCCGCGTGGGCAACAAGGCCTTCGCCGA<br>GTTCGTGACCAACCAGGCCGGCGGCGAGTACCGCCTGACCCACAGCG<br>CCGACCCCATCCCCCGCCTGCCCCCATCATCTTCAACTACCGCCACA<br>CCAGCCCCGAGTACTGGTTCGACGAGGGCGAGGACGGCGTGGTGAC<br>CGTGGACGAGTTCCAGATCTGCGAGGGCTACGCCAACGTGAACTGCA<br>ACGCCGCCACCAGCGGCTTCAACATGGACCTGCACGGCTGGTACTTC<br>CAGAACCACCAGGGCTGCAGCCTGGGCTACACCCCCTGGCGCGCCGT<br>GAAGGAGCGCGAGCTGAGCGACCCCGAGCTGGAGGCCCTGGTGAAC<br>CGCTTCGCCGAGATGGACAAGGCCTACGTGGAGAACCTGAACCTGGA<br>GGGCCTGGAGCCC |
| SEQ ID NO 5<br>(DNA) PH3<br>[*Meiothermus ruber*] | ATGGGCAAGCCCATGCGCTTCGCCGTGGGCATCCTGGCCCTGCTGCT<br>GGCCGCCTGCAGCCAGCCCGCCACCGAGAGCACCAGCGCCAGCATC<br>GTGGAGGACATGCGCCAGCTGGGCGTGGAGCCCGAGGCCATCGCCG<br>CCTACACCGAGGCCCTGCAGAACCTGGAGCAGGCCCGCCTGGCCCTG<br>CAGAGCCTGGGCGCCGGCGACCTGCTGCTGGTGCAGAGCATCGCCCT<br>GGGCAGCGTGGCCAACTACGACGCCTACTACAACGCCCGCGCCAGCT<br>ACCCCCAGTTCGACTGGAGCCGCAACGGCTGCAGCGCCCCCGAGGG<br>CCTGGGCCTGGGCTACCGCGAGACCTTCCGCCCCGCCTGCAACGTGC<br>ACGACTTCGGCTACGCCAACTTCCCCCGCTTCCCCAGCCTGTACAACG<br>AGACCGGCCGCAAGCTGAGCGACGACAACTTCCTGGTGAACATGAAC<br>CAGATCTGCCGCCCCCGCAGCTTCCTGAGCCGCAGCGCCTGCTACAG<br>CGCCGCCTACGCCTACTACCTGGCCGTGCGCAGCGCCGGCTGGGCCT<br>ACTTCTACGAC |
| SEQ ID NO 6<br>(DNA) PH4<br>[*Meiothermus silvanus*] | ATGCGCGTGGTGCTGCTGATGCTGGTGCTGGTGCTGGCCGCCTGCGG<br>CAGCCAGACCGGCGCCCCCAACTGGACCCTGGAGCAGATCGCCGCC<br>CTGACCCCCGAGCAGATCGACGCCCTGAGCGAGGGCGAGCTGCAGAA<br>GATCCAGACCATCCTGCAGCCCGAGTTCGCCCGCGTGGAGAGCCAGC<br>TGATCCAGCTGCAGAGCCAGCTGGAGGCCCTGGTGGCCGCCCAGGAC<br>AGCCGCTGGCCCAACTTCGACTACACCGTGTACCTGGCCACCGCCAT<br>CCCCTACGGCACCTTCTTCACCTACTACCGCACCTACAGCGGCCCCGA<br>CTGGAGCAACGACGGCTGCAGCTACAGCCCCGACAAGCCCCTGTTCC<br>TGAACTTCAAGGACCCCTGCAACCACCACGACTTCGGCTACCGC |

In a particular embodiment the improver as disclosed herein provides that said enzyme is a lipolytic enzyme with phospholipase activity from *Chaetomium thermophilum*, preferably an enzyme with SEQ ID NO 1, or a close variant thereof. In a particular embodiment the improver as disclosed herein provides that said enzyme is a lipolytic enzyme with phospholipase activity from *Meiothermus ruber*, preferably an enzyme with SEQ ID NO 2, or a close variant thereof. In a particular embodiment the improver as disclosed herein provides that said enzyme is a lipolytic enzyme with phospholipase activity from *Meiothermus silvanus*, preferably an enzyme with SEQ ID NO 3, or a close variant thereof.

In the context of the present invention a "close variant" as referred to herein is an enzyme that improves (the quality of) baked products as described above and that share a significant identity with SEQ ID NO 1 to 3. "Significant identity" in the context of the present invention refers to at least 85% identity, preferably at least 90% identity, preferably at least 91%, more preferably at least 92%, 93%, 94%, 95%, 96%, 97%, 98% or even at least 99% with SEQ ID NO 1 to 3.

The relatedness between two amino acid sequences or between two nucleotide sequences is described by the parameter "identity". For present purposes, the degree of identity between two amino acid sequences is determined as in WO 2010/0142 697 using the Needleman-Wunsch algorithm as implemented in the Needle program of the EMBOSS package, preferably version 3.0.0 or later. The optional parameters used are gap open penalty of 10, gap extension penalty of 0.5, and the EBLOSUM62 (EMBOSS version of BLOSUM62) substitution matrix. The output of Needle labelled "longest identity" (obtained using the— nobrief option) is used as the percent identity and is calculated as follows: (Identical Residues×100)/(Length of Alignment−Total Number of Gaps in Alignment).

In a particular embodiment the improver composition as disclosed herein provides that said phospholipase retains more than 40% of its phospholipase activity after being incubated for 60 minutes at 50° C., preferably more than 50% of its activity after being incubated for 60 minutes at 50° C.

The activity is measured by determining the phospholipase activity as indicated herein (using p-nitrophenyl phosphorylcholine as substrate).

In still preferred embodiments the improver composition as provided herein comprises a phospholipase having the amino acid sequence of SEQ ID NO 1, of SEQ ID NO 2, of SEQ ID NO 3, preferably of SEQ ID NO 2 or 3, more preferably of SEQ ID NO 3, or of close variants thereof, wherein said phospholipase is characterized by having a phospholipase A1 activity/phospholipase A2 activity ratio ranging between 0.01 and 100, preferably ranging between 0.01 and 80, more preferably ranging between 0.01 and 50, more preferably ranging between 0.01 and 10, even more preferably ranging between 1 and 50, even more preferably ranging between 1 and 10; and having a phospholipase optimum temperature of 45° C. or more.

In still preferred embodiments the improver composition as provided herein comprises a phospholipase having the amino acid sequence of SEQ ID NO 1 or close variants thereof, wherein said phospholipase is characterized by having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

In still preferred embodiments the improver composition as provided herein comprises a phospholipase having the amino acid sequence of SEQ ID NO 2 or close variants thereof, wherein said phospholipase is characterized by having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

In still preferred embodiments the improver composition as provided herein comprises a phospholipase having the amino acid sequence of SEQ ID NO 3 or close variants thereof, wherein said phospholipase is characterized by having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

In a particular embodiment the improver composition as disclosed herein is a bread improver composition or a patisserie mix or premix.

The composition of the present invention may advantageously be part of a bread improver or a patisserie mix or premix. "Bread improvers" (also referred to as "dough improvers" or "improving agent" or "flour treatment agent") are typically added to the dough during baking in order to improve texture, volume, flavour and freshness of the baked product as well as to improve machinability and stability of the dough. Typically, a bread improver comprises or consists of: one or more enzymes (such as e.g. amylases (alpha-amylases, beta-amylases, glucoamylases, raw starch degrading amylases), xylanases (hemicellulases), cellulases, pectinases, proteases, pectate lyases, oxidases (peroxidases, glucose oxidase, pyranose oxidases, hexose oxydases, L-amino acid oxidases, carbohydrate oxidases, sulfurhydryl oxidases), lipoxygenases, dehydrogenases, laccases, transglutaminases, acyltransferases, protein disulfide isomerases), one or more oxidizing or reducing agents (such as e.g. ascorbic acid, glutathione, cysteine), one or more emulsifiers (such as e.g. diacetyl tartaric acid esters of monoglycerides (DATEM), sodium stearoyl lactylate (SSL), calcium stearoyl lactylate (CSL), glycerol monostearate (GMS), rhamnolipids, lecithins, sucroesters, bile salts), one or more lipid materials (such as e.g. margarine, butter, oil, shortening), one or more vitamins (such as e.g. pantothenic acid and vitamin E), one or more gums, and/or one or more sources of fibre (such as e.g. oat fibre). Cake (patisserie) mixes typically comprise all the ingredients of a cake recipe with the exception of water, fat (oil, butter, margarine) and eggs. Cake premixes are typically cake mixes where all or part of the flour and sugar has been removed.

In particular embodiments the composition comprises one or more phospholipase having a low phospholipase A1 activity/phospholipase A2 activity ratio as described above and at least one, preferably two, additional ingredients chosen from the list of enzyme(s), oxidizing agent(s), reducing agent(s), emulsifier(s), lipid(s), vitamin(s), fibre(s). The inventors have found that it was particularly advantageous to include in the composition one or more enzyme(s) chosen from the group of amylases (alpha-amylases, beta-amylases, glucoamylases, raw starch degrading amylases), xylanases (hemicellulases), cellulases, pectinases, proteases, pectate lyases, oxidases (peroxidases, glucose oxidase, pyranose oxidases, hexose oxydases, L-amino acid oxidases, carbohydrate oxidases, sulfurhydryl oxidases), lipoxygenases, dehydrogenases, laccases, transglutaminases, acyltransferases, protein disulfide isomerases.

Furthermore, in a further aspect, the present invention relates to the use of a phospholipase in bakery applications, wherein said phospholipase has a phospholipase A1 activity/ phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

In a particular embodiment the use of the composition as disclosed herein is provided wherein said phospholipase has a sequence identity of at least 85% with any of SEQ ID NO 1, SEQ ID NO 2 and/or SEQ ID NO 3, preferably at least 85% with SEQ ID NO 2 and/or 3, more preferably at least 85% with SEQ ID NO 3.

In a particular embodiment the use of the composition as disclosed herein in bread or patisserie products is provided.

Preferably, when the use of the composition as disclosed herein is the preparation of bread, said phospholipase has a sequence identity of at least 85% with SEQ ID NO 1 and/or SEQ ID NO 2, more preferably of at least 85% with SEQ ID NO 1.

In a particular embodiment the use of the composition as disclosed herein in the preparation of cakes is provided.

Preferably, when the use of the composition as disclosed herein is the preparation of cakes, said phospholipase has a sequence identity of at least 85% with SEQ ID NO 1 and/or SEQ ID NO 3, more preferably of at least 85% with SEQ ID NO 3.

Disclosed herein are also methods for preparing baked products wherein an enzyme having a low phospholipase A1 activity/phospholipase A2 activity ratio is used in the preparation method.

Furthermore, in a further aspect, the present invention relates to a method for preparing a baked product, comprising the steps of adding to the dough or batter, prior to baking, a phospholipase having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

In a particular embodiment the phospholipase retains more than 40%, preferably more than 50% of its phospholipase activity after 60 minutes at 50° C.

In said method the lipase activity is expressed in milliunits (LmU) that is defined as the amount of enzyme needed to release one nanomole (nmole) per minute of p-nitrophenol from p-nitrophenyl palmitate at 40° C. and pH 7.5, the phospholipase A1 activity is expressed in milliunits (PA1 mU) that is defined as the amount of enzyme that hydrolyses one nanomole (nmole) per minute of fluorescent fatty acid substituted at the sn-1 position of N-((6-(2,4-DNP)Amino) Hexanoyl)-1-(BODIPY®FL C5)-2-Hexyl-Sn-Glycero-3-Phosphoethanolamine at 40° C. and pH7.4 and the phospholipase A2 activity is expressed in milliunits (PA2 mU) per minute that is defined as the amount of enzyme that hydrolyses one nanomole (nmole) of fluorescent fatty acid substituted at the sn-2 position of 1-O-(6-BODIPY®558/568-Aminohexyl)-2-BODIPY®FL C5-Sn-Glycero-3-Phosphocholine at 40° C. and pH 8.9, wherein BODIPY® is generically known as 4,4-difluoro-4-bora-3a,4a-diaza-s-indacene, and the phospholipase activity is expressed in milliunits (PmU) that is defined as the amount of enzyme needed to release one nanomole (nmol) per minute of p-nitrophenol from p-nitrophenyl phosphorylcholine per minute at 50° C. and pH7.5.

In a particular embodiment the method as disclosed herein provides that said dough or batter comprises between 5000 and 100000 PmU/100 kg flour, preferably between 7000 and 70000 PmU/100 kg flour, more preferably between 10000 and 60000 PmU/100 kg flour of said phospholipase.

The method as disclosed herein advantageously allows to improve the batter or the dough tolerance and/or to improve the baked products properties, such as the volume or the freshness.

In a particular embodiment the method as disclosed herein provides that said dough or batter shows improved tolerance.

The inventors have found that the use of a particular enzyme as disclosed herein, in bakery applications has an improved effect on dough or batter tolerance.

In the present context the dough or batter tolerance refers to the capacity of a dough or a batter to maintain its shape in stress conditions such a prolonged proofing time or mechanical shocks during or after proofing and to provide, after baking, a baked product with properties (e.g. volume) comparable to an baked product obtained with an unstressed dough or batter.

In a particular embodiment the method as disclosed herein provides that said baked product shows improved freshness.

In the present context freshness refers to a combination of texture parameters such as softness, moistness, cohesiveness, gumminess and resiliency. Loss of freshness is usually associated with staling. More particularly an improved freshness of a baked product corresponds to an improved softness and/or an improved moistness and/or an improved short bite when compared to a reference. These parameters may be advantageously measured by physical methods such as with a texturometer or by sensorial analysis conducted with a panel of expert judges.

Disclosed herein are also baked products comprising an enzyme having a low phospholipase A1 activity/phospholipase A2 activity ratio.

Furthermore, in a further aspect, the present invention relates to a baked product prepared from a dough or batter comprising the composition as disclosed herein.

In the context of the present invention a baked product is a bakery or patisserie product known in the art, such as for instance those selected from the group comprising bread, soft rolls, bagels, donuts, Danish pastry, hamburger rolls, pizza, pita bread, ciabatta, sponge cakes, cream cakes, pound cakes, muffins, cupcakes, steamed cakes, waffles, brownies, cake donuts, yeast raised donuts, baguettes, rolls, crackers, biscuits, cookies, pie crusts, rusks and other baked products. More preferably the present invention refers to bread, baguettes and rolls.

A further object of the present invention relates to the use of compositions, bread improvers, patisserie mixes and/or patisserie premixes to prepare baked products.

Furthermore, in a further aspect, the present invention relates to a baked product prepared from a dough or batter comprising a phospholipase having a phospholipase A1 activity/phospholipase A2 activity ratio ranging between 0.01 and 100, preferably ranging between 0.01 and 80, more preferably ranging between 0.01 and 50, even more preferably ranging between 1 and 50, even more preferably ranging between 2 and 50, even more preferably ranging between 0.01 and 25, even more preferably ranging between 1 and 25, and even more preferably ranging between 2 and 25, more preferably ranging between 0.01 and 10, even more preferably ranging between 1 and 10; and having a phospholipase optimum temperature of 45° C. or more.

EXAMPLES

Example 1: Enzymatic Activities Determination

Lipase:

The lipase activity is measured using p-nitrophenyl palmitate (pNPP) as substrate. The release of yellow p-nitrophenol due to hydrolysis of p-nitrophenyl palmitate by lipase is measured by spectrophotometry at 414 nm. One lipase milliunit (LmU) is defined as the amount of enzyme needed to release one nanomole (nmole) per minute of p-nitrophenol from p-nitrophenyl palmitate at 40° C. and pH 7.5. To perform the test, 120 µl of 1 mM pNPP solution (dissolved in 0.05 M Na-phosphate buffer at pH 7.5 containing 0.69 M acetone and 0.0049 M Triton X-100) are mixed with 60 µl of enzyme sample and incubated at 40° C. for 30 min. The absorbance is measured at 414 nm against a substrate blank in 96-wells microplates.

The activity is expressed as: LmU/ml=(((Abs enzyme−Abs blank)/30)×0.18))/(13380×0.06))×sample dilution×1000000 [30=reaction time in minutes; 0.18=reaction volume in ml; 13380=molar extinction coefficient at 414 nm ($M^{-1}$ $cm^{-1}$); 0.06=enzyme sample volume in ml; 1000000 to convert in LmU/ml]

Phospholipase:

The phospholipase activity is measured using p-nitrophenyl phosphorylcholine (pNPPC) as substrate. The release of yellow p-nitrophenol due to hydrolysis of p-nitrophenyl phosphorylcholine by phospholipase is measured by spectrophotometry at 414 nm. One phospholipase milliunit (PmU) is defined as the amount of enzyme needed to release 1 nmol of p-nitrophenol per minute at 50° C. and pH7.5. To perform the test, 120 µl of 0.02 M pNPPC solution (dissolved in 0.05 M Na-phosphate buffer at pH 7.5 containing 0.69 M acetone and 0.0049 M Triton X-100) are mixed with 60 µl of enzyme sample and incubated at 50° C. for 30 min. Afterwards, 720 µl of 1M $Na_2CO_3$ are added to stop the reaction. The absorbance is measured at 414 nm against a substrate blank in 96-wells microplates.

The activity is expressed as: PmU/ml=(((Abs enzyme−Abs blank)/30)×0.9))/(13380×0.06))×sample dilution×1000000

[30=reaction time in minutes; 0.9=reaction volume in ml; 13380=molar extinction coefficient at 414 nm ($M^{-1}$ $cm^{-1}$); 0.06=enzyme sample volume in ml; 1000000 to convert in PmU/ml]

Phospholipase A1:

The phospholipase A1 (PLA1) activity is measured using a lipid mix of 16.5 µM dioleoylphosphatidylcholine, 16.5 µM dioleoylphosphatidylglycerol and 3.3 µM dye labelled N-((6-(2,4-DNP)Amino)Hexanoyl)-1-(BODIPY®FL C5)-2-Hexyl-Sn-Glycero-3-Phosphoethanolamine (PED-A1) as substrate (obtained in the EnzChek Phospholipase A1 assay kit-ThermoFisher Scientific, wherein BODIPY® is generically known as 4,4-difluoro-4-bora-3a,4a-diaza-s-indacene). The PED-A1 is specific for PLA1 and is a dye-labelled glycerophosphoethanolamine with BODIPY®FL dye-labelled acyl chain at the sn-1 position and dinitrophenyl quencher-modified head group. One phospholipase A1 milliunit (PA1 mU) is defined as the amount of enzyme needed to release one nanomole (nmole) per minute of fluorescent fatty acid substituted at the sn-1 position of PED-A1 at 40° C. and pH7.4 (wherein BODIPY® is generically known as 4,4-difluoro-4-bora-3a,4a-diaza-s-indacene). The test is performed in 96-wells microplates using a total volume of 100 µl per well. Different lipid solutions were prepared in reaction buffer containing 250 mM Tris-HCl, 0.7 M NaCl and 10 mM $CaCl_2$) at pH 7.4. Samples and controls are mixed with the lipid-mix at a ratio of 1:1 (50 µl sample/control and 50 µl lipid mix). The enzymatic reaction is performed at 40° C. during 30 min. A calibration curve is established by use of different concentrations of phospholipase A1 provided in the kit (Lecitase ultra). The fluorescence measurement is performed with excitation at 480 nm and with emission at 515 nm.

The activity is expressed as: PA1 mU/ml=(((fluorescence intensity enzyme−fluorescence intensity blank)−intercept value)/slope value of calibration curve)×sample dilution×1000 [1000 to convert in PA1 mU/ml]

Phospholipase A2:

The phospholipase A2 (PLA2) activity is measured using a lipid mix of 16.5 µM dioleoylphosphatidylcholine, 16.5 µM dioleoylphosphatidylglycerol and 1.7 µM dye labelled 1-O-(6-BODIPY®558/568-Aminohexyl)-2-BODIPY® FL C5-Sn-Glycero-3-Phosphocholine (Red/Green BODIPY® PC-A2) as substrate (obtained in the EnzChek Phospholipase A2 assay kit-ThermoFisher Scientific, wherein BODIPY® is generically known as 4,4-difluoro-4-bora-3a,4a-diaza-s-indacene). The Red/Green BODIPY® PC-A2 substrate is selective for PLA2 and provides sensitive and continuous rapid real-time monitoring of PLA2 enzyme activities. One phospholipase A2 milliunit (PA2 mU) is defined as the amount of enzyme needed to release one nanomole (nmole) per minute of fluorescent fatty acid substituted at the sn-2 position of Red/Green BODIPY® PC-A2 at 40° C. and pH 8.9 (wherein BODIPY® is generically known as 4,4-difluoro-4-bora-3a,4a-diaza-s-indacene). The test is performed 96-wells microplates using a total volume of 100 µl per well. Different lipid solutions were prepared in reaction buffer containing 250 mM Tris-HCl, 500 mM NaCl and 5 mM $CaCl_2$) at pH 8.9. Samples and controls are mixed with lipid-mix at a ratio of 1:1 (50 µl sample/control and 50 µl lipid mix). The enzymatic reaction is performed at 40° C. during 10 min. A calibration curve is established by use of different concentrations of phospholipase A2 from honey bee venom provided in the kit. The fluorescence measurement is performed with excitation at 480 nm and with emission at 515 nm.

The activity is expressed as: PA2 mU/ml=(((fluorescence intensity enzyme−fluorescence intensity blank)−intercept value)/slope value of calibration curve)×sample dilution×1000 [1000=PA2 mU/ml]

Example 2: Enzymes

The following enzymes were used in the following examples.

Lipolytic enzyme with phospholipase activity from *Chaetomium thermophilum* (PH2) having the SEQ NO 1 amino acid sequence.

Lipolytic enzyme with phospholipase activity from *Meiothermus ruber* (PH3) having the SEQ NO 2 amino acid sequence.

Lipolytic enzyme with phospholipase activity from *Meiothermus silvanus* (PH4) having the SEQ NO 3 amino acid sequence.

LIPOPAN® F (lipase from *Fusarium oxysporum*; Novozymes) (LIF)

LIPOPAN® Max (lipase from *Thermomyces lanuginosus*; Novozymes) (LIM)

CAKEZYME® SMART (lipase from porcine pancreas; DSM) (CAK)

The PH2, PH3 and PH4 enzymes have been obtained by cloning and expressing the corresponding genes as described hereafter. The other enzymes were obtained from their respective suppliers.

Cloning of the PH2, PH3 and PH4 Genes

Based on the identified sequences of putative lipolytic enzymes genes the DNA sequence coding for the enzymes have been synthesized in order to be expressed into the pET22b plasmid by using the pelB leader sequence and following standard protocols.

The DNA sequences corresponding to PH2, PH3 and PH4 are shown in Table A and are respectively SEQ ID NO 4, SEQ ID NO 5 and SEQ ID NO 6 (see table A).

The complete synthesized DNA fragments were subcloned into a pUC19 derivative plasmid.

These plasmids were used to transform *E. coli* DH5α® ultracompetent cells. Purified plasmid preparations made with the Pure Yield Midiprep System (Promega) were digested by using appropriate restriction enzymes to isolate the DNA fragment containing the lipolytic enzymes coding sequences. Those fragments were subcloned into the pET 22b(+) cloning vector (Novagen) and the resulting recombinant plasmids were transformed in *E. coli* BL21 (DE3) cells (Agilent Technologies). Purified plasmid preparations made with the Pure Yield Midiprep System (Promega) were sequenced by using a AB13700 DNA sequencer (Applied Biosystems). Sequencing of the inserted fragments was carried out using the universal primers T7 promoter and T7 terminator as well as primers corresponding to internal DNA sequences. The sequences obtained were identical to the expected sequences.

Cultures of the Recombinant Strains and Production of PH2, PH3 and PH4

15 ml of a 5 hours preculture (37° C.) of the *E. coli* BL21 (DE3) cells carrying the lipolytic enzyme genes were centrifuged at 10000 g for 1 minute and the pellet was resuspended in 500 ml Terrific broth (12 g/l Bacto tryptone (Difco), 24 g/l yeast extract (Difco), 4 ml/glycerol, 12.54 g/l $K_2HPO_4$, 2.31 g/l $KH_2PO_4$) containing 200 μg/ml ampicillin in a 2 liters shake flask. The cultures were incubated at 37° C. and 250 rpm until an absorbance at 550 nm of between 3 & 4 was reached whereupon the expression of the enzyme was induced with 1 mM isopropyl-1-thio-β-galactopyranoside.

Recovery of PH2, PH3 and PH4

After 15 hours incubation at 37° C. the cells were harvested by centrifugation at 18000 g for 30 minutes at 4° C., resuspended in 50 mM BICINE containing 10 mM NaCl, disrupted in a prechilled cell disrupter (Panda 2K, Niro Soavi, GEA Process Engineering Division) at 1500 bars and centrifuged at 40,000 g for 30 minutes. Chromosomal DNA was removed from the crude cell lysates by treatment with 0.2% protamine sulfate (Calbiochem) and centrifugation at 40,000 g for 30 minutes. 25 units of benzonase (Merck, Darmstadt, Germany) were then added to the solution.

After such a treatment the lipolytic enzyme preparations have been clarified by an end filtration on a Millipore POD system with a range of cut-off from 0.05 to 1 μm then concentrated by ultrafiltration on a cross flow filtration system (Satocon-Sartorius) with a cut-off of 5 kDa. The concentrated enzyme solutions was filtered on a sterile filtration system, including end filtration of 0.8 and 0.22 μm (absolute filter).

The lipases and phospholipases activities of the enzymes have been determined using the protocols of example 1. The results are shown in table 1.

TABLE 1

| Enzyme | PL activity (PmU/ml) | PLA1 activity (PA1 mU/ml or g) | PLA2 activity (PA2 mU/ml or g) | Lipase activity (L) (LmU/ml) | PLA1/PLA2 | PLA1/L |
|---|---|---|---|---|---|---|
| PH2 | 140 | 13 | 450 | 11 | 0.03 | 1 |
| PH3 | 27 | 111406 | 31634 | 16 | 3.52 | 6963 |
| PH4 | 33 | 94400 | 14732 | 15 | 6.41 | 6293 |
| LIF | 50 | 6532478 | 13367 | 788113 | 489 | 8 |
| LIM | 0.4 | 94410920 | 4512 | 10913 | 20920 | 8650 |
| CAK | 7 | 378051 | 2035471 | 45 | 0.186 | 8401 |

The activity of the enzymes in function of the temperature has been determined using the phospholipase assay of example 1 except for the temperature of the test. Results are presented in Table 2.

TABLE 2

| | Activity (% of maximum activity) | | | |
|---|---|---|---|---|
| Enzyme | 30° C. | 40° C. | 50° C. | 60° C. |
| PH2 | 23 | 84 | 100 | 34 |
| PH3 | 40 | 75 | 100 | 92 |
| PH4 | 50 | 67 | 93 | 100 |
| LIM | 83 | 100 | 50 | 33 |
| LIF | 73 | 100 | 42 | 28 |
| CAK | 65 | 100 | 75 | 59 |

The stability of the enzymes has been determined by preincubating a sample of the enzyme at 50° C. for 30, 60 and 240 minutes before performing the phospholipase assay as in example 1. Results are presented in Table 3.

TABLE 3

| | residual activity (%) | | |
|---|---|---|---|
| Enzyme | 30 min | 60 min | 240 min |
| PH2 | 106 | 102 | 64 |
| PH3 | 59 | 52 | 41 |
| PH4 | 87 | 86 | 95 |

Example 3: Sponge Cakes

Sponge cakes were made using a typical batter cake recipe: 23.4% eggs, 25.2% flour, 7.5% starch, 2.1% vegetable fat, 22.3% sugar (monosaccharides, disaccharides, polyols), 1.9% skimmed milk powder, 1.1% baking powder (sodium bicarbonate and SAPP (sodium acid pyrophosphate) or sodium aluminium pyrophosphate), 3.2% cake gel (emulsifiers), and water to 100%.

Enzymes were first added to the dry ingredients. The liquid ingredients (eggs, water, glycerol, . . . ) were then added to the mix. All ingredients were mixed together for 5 min at high speed in an Hobart mixer. The batter were whipped until a batter density of about 300 to 600 grams per litre. Four sponge cake batters of 900 g were prepared per test and baked at a temperature of 180° C. for 30 minutes. Afterwards the sponge cakes were cooled at room temperature and packed in a plastic bag.

The volume of the cakes was evaluated by the rapeseed displacement method. The height of the cakes was evaluated by using a calliper.

Textural properties (hardness, cohesiveness and springiness) of the cakes were measured 1, 14 and/or 21 days after baking by Texture Profile Analysis (TPA) using a TAXTplus device (Stable Micro Systems).

Two consecutive deformations of a cylindrical crumb sample ($\phi$=45 mm) performed with a cylindrical probe ($\phi$=100 mm) with a maximum deformation of 50% of the initial height of the product are performed at a deformation speed of 2 mm/s and waiting time between consecutive deformations of 3 s. Force is recorded as a function of time.

Hardness is measured as the force of the probe to the crumb necessary to make the first deformation (height of the $1^{st}$ peak).

Cohesiveness is calculated as the ratio (expressed in percent) between the surface under the second deformation curve (downwards+upwards) and the surface under the first deformation curve (downwards+upwards).

TABLE 4

| Enzyme | | Hardness (=Softness) | | Cohesiveness | | Volume (cm³) | Height (mm) |
|---|---|---|---|---|---|---|---|
| Type | Dosage/ 100 kg flour | Day 1 | Day 14 | Day 1 | Day 14 | Day 1 | Day 1 |
| none | — | 377 | 931 | 59.16 | 40.64 | 1800 | 68 |
| LIM | 7 g* | 371 | 945 | 58.77 | 40.88 | 1825 | 70.5 |
| LIF | 7 g* | 387 | 855 | 58.77 | 44.48 | 1800 | 68.1 |
| PH2 | 60000 PmU | 377 | 835 | 60.33 | 42.64 | 1850 | 68.5 |
| PH3 | 60000 PmU | 374 | 858 | 58.58 | 40.53 | 1800 | 68.1 |
| PH4 | 60000 PmU | 308 | 785 | 58.54 | 40.64 | 1900 | 73.1 |

*Dosage recommended by the enzyme supplier

The results show that the use of enzymes according to the invention improves the softness without adverse effect on the volume and the height of the cakes.

Cake texture parameters were further evaluated by performing a sensorial analysis using a panel of cake experts. The cake experts are cake consumers that have been trained to describe and score the different cake texture properties that describe cake freshness: softness, moistness and cohesiveness, all individually and independently. The cake experts used a score card with a scale with scores between 1 and 9 for each parameter. For softness a score of 1 indicates an extremely hard cake, difficult to bite, and a score of 9 indicates an extremely soft cake, with very much less force needed to bite the cake crumb. For moistness, a score of 1 indicates an extremely dry cake crumb and a score of 9 indicates an extremely moist cake. For cohesiveness a score of 1 indicates a very crumbly cake and a score of 9 indicates a very cohesive cake that remains in one piece. Sensorial analyses are calibrated and a value difference of 0.5 is considered as significant.

The results of the sensorial evaluation are presented in table 5.

TABLE 5

|  | moistness | softness | short bite |
|---|---|---|---|
| No enzyme | 3.25 | 5 | 4.75 |
| LIF 7 g | 4 | 5.125 | 4.25 |
| LIM 7 g | 3.5 | 5 | 4.25 |
| PH2 60 000 PmU | 5.125 | 5.5 | 6.25 |
| PH3 60 000 PmU | 5.2 | 6 | 5.5 |
| PH4 60 000 PmU | 4.8 | 6 | 4.75 |

The results show that the use of an enzyme according to the invention give cakes with improved texture parameters.

Example 4: Crusty Rolls

Effect of lipolytic enzymes with phospholipase activity in crusty rolls making Crusty rolls were prepared using the dough compositions of Table 6.

TABLE 6

|  | Ref | Test1 | Test2 | Test3 | Test4 |
|---|---|---|---|---|---|
| Ingredients (grams) | | | | | |
| Wheat Flour (Crousti; Belgium)) | 2100 | 2100 | 2100 | 2100 | 2100 |
| Water | 1260 | 1260 | 1260 | 1260 | 1260 |
| Fresh Yeast (Bruggeman, Belgium) | 126 | 126 | 126 | 126 | 126 |

TABLE 6-continued

|  | Ref | Test1 | Test2 | Test3 | Test4 |
|---|---|---|---|---|---|
| Sodium Chloride | 42 | 42 | 42 | 42 | 42 |
| Bread improver* | 21 | 21 | 21 | 21 | 21 |
| Enzymes | | | | | |
| PH2 (PmU) | | 315 | | | |
| PH3 (PmU) | | | 315 | | |
| PH4 (PmU) | | | | 315 | |
| Lipopan Max (grams) | | | | | 0.315 |

The ingredients were mixed for 2 min at low and 5 min at high speed in an Eberhardt N24 mixer. The final dough temperature as well as the resting and proofing temperatures were 25° C. After resting for 15 min at 25° C., the dough was reworked manually and rested for another 10 min. Afterwards, 2 kg dough pieces were made up and proofed for 10 min. The 2-kg dough pieces were divided and made up using the Rotamat. 50 gr. round dough pieces were obtained. After another 5 min resting time, the dough pieces were cut by pressing and submitted to a final proofing stage at 35° C. for 120 min or for 120 min after a shock test. The shock test was applied to the proofed dough as follows: after the second proof and before baking the tray containing the doughs is dropped from a height of 10 cm. The dough pieces were baked at 230° C. in a MIWE Roll-In oven with steam (Michael Wenz-Arnstein-Germany). The volume of 6 rolls was measured using the commonly used rapeseed displacement method. The results are presented in Table 7.

TABLE 7

|  | Rolls volume (ml per 6) | | | | |
| --- | --- | --- | --- | --- | --- |
|  | Ref | Test1 | Test2 | Test3 | Test4 |
| 120 min proofing | 1850 | 2075 | 2150 | 2050 | 2150 |
| 120 min proofing + Shock test | 1350 | 1675 | 1675 | 1500 | 1550 |

TABLE 7-continued

|  | Rolls volume (ml per 6) | | | | |
| --- | --- | --- | --- | --- | --- |
|  | Ref | Test1 | Test2 | Test3 | Test4 |
| % loss of volume with shock test | −27 | −19 | −22 | −27 | −28 |

The results show that the use of an according to the invention gives a better dough tolerance compared to the reference and compared to a commercially available enzyme.

The invention claimed is:

1. A method for preparing a baked product, comprising the steps of adding to a dough or batter, prior to baking, a phospholipase having a phospholipase A1 activity/phospholipase A2 activity ratio ranging between 0.01 and 100, between 0.01 and 80, between 0.01 and 50, between 0.01 and 25, between 0.01 and 10, or between 1 and 10 and having a phospholipase optimum temperature of 45° C. or more; wherein said phospholipase has a sequence identity of at least 95% with SEQ ID NO: 2 or SEQ ID NO: 3.

2. The method of claim 1, wherein said dough or batter comprises between 5000 and 100000 PmU/100 kg flour, between 7000 and 70000 PmU/100 kg flour, or between 10000 and 60000 PmU/100 kg flour of said phospholipase.

3. The method of claim 1, wherein said dough or batter has improved tolerance compared to a dough or batter without said phospholipase.

4. The method of claim 1, wherein the baked product is bread or a patisserie product.

5. The method of claim 1, wherein the baked product is a cake.

* * * * *

SEQUENCE LISTING

<160> NUMBER OF SEQ ID NOS: 6

<210> SEQ ID NO 1
<211> LENGTH: 333
<212> TYPE: PRT
<213> ORGANISM: Chaetomium thermophilum

<400> SEQUENCE: 1

```
Met Lys Gly Phe Leu Leu Ala Ser Leu Ala Ala Leu Ala Val Ala Ala
1               5                   10                  15

Pro Ser Ser Lys Lys Gln Arg Ala Ala Pro Val Thr Ala Gln Gln Leu
            20                  25                  30

Asn Asn Phe Lys Leu Tyr Met Gln Trp Ser Ser Ala Ser His Cys Ala
        35                  40                  45

Asn Glu Ala Pro Ile Gly Ser Val Val Thr Cys Thr Asp Asn Gln Cys
    50                  55                  60

Ser Met Phe Gln Ser His Asn Ala Thr Val Ala Ala Thr Phe Ile Gly
65                  70                  75                  80

Ser Ile Leu Asp Met Arg Gly Phe Leu Gly Ile Asp Asp Val Asp Lys
                85                  90                  95

Asn Ile Val Leu Ser Phe Arg Gly Ser Thr Ser Trp Arg Asn Trp Ile
            100                 105                 110

Ala Asp Ala Ile Phe Val Gln Thr Pro Cys Asp Leu Thr Pro Gly Cys
        115                 120                 125

Leu Val His Ala Gly Phe Tyr Ala Ser Trp Leu Glu Ile Lys Asn Ser
    130                 135                 140

Val Ile Asp Ala Val Lys Ala Ala Lys Ala Ala His Pro Asn Tyr Lys
145                 150                 155                 160

Leu Val Thr Thr Gly His Ser Leu Gly Ala Ala Val Ala Thr Leu Ala
                165                 170                 175

Ala Ala Thr Leu Arg Lys Ala Gly Ile Pro Ile Glu Leu Tyr Thr Tyr
            180                 185                 190

Gly Ser Pro Arg Val Gly Asn Lys Ala Phe Ala Glu Phe Val Thr Asn
        195                 200                 205

Gln Ala Gly Gly Glu Tyr Arg Leu Thr His Ser Ala Asp Pro Ile Pro
    210                 215                 220

Arg Leu Pro Pro Ile Ile Phe Asn Tyr Arg His Thr Ser Pro Glu Tyr
225                 230                 235                 240
```

-continued

Trp Phe Asp Glu Gly Glu Asp Gly Val Val Thr Val Asp Glu Phe Gln
                245                 250                 255

Ile Cys Glu Gly Tyr Ala Asn Val Asn Cys Asn Ala Ala Thr Ser Gly
            260                 265                 270

Phe Asn Met Asp Leu His Gly Trp Tyr Phe Gln Asn His Gln Gly Cys
        275                 280                 285

Ser Leu Gly Tyr Thr Pro Trp Arg Ala Val Lys Arg Glu Leu Ser
    290                 295                 300

Asp Pro Glu Leu Glu Ala Leu Val Asn Arg Phe Ala Glu Met Asp Lys
305                 310                 315                 320

Ala Tyr Val Glu Asn Leu Asn Leu Glu Gly Leu Glu Pro
                325                 330

<210> SEQ ID NO 2
<211> LENGTH: 191
<212> TYPE: PRT
<213> ORGANISM: Meiothermus ruber

<400> SEQUENCE: 2

Met Gly Lys Pro Met Arg Phe Ala Val Gly Ile Leu Ala Leu Leu Leu
1               5                   10                  15

Ala Ala Cys Ser Gln Pro Ala Thr Glu Ser Thr Ser Ala Ser Ile Val
            20                  25                  30

Glu Asp Met Arg Gln Leu Gly Val Glu Pro Glu Ala Ile Ala Ala Tyr
        35                  40                  45

Thr Glu Ala Leu Gln Asn Leu Glu Gln Ala Arg Leu Ala Leu Gln Ser
    50                  55                  60

Leu Gly Ala Gly Asp Leu Leu Val Gln Ser Ile Ala Leu Gly Ser
65                  70                  75                  80

Val Ala Asn Tyr Asp Ala Tyr Tyr Asn Ala Arg Ala Ser Tyr Pro Gln
                85                  90                  95

Phe Asp Trp Ser Arg Asn Gly Cys Ser Ala Pro Glu Gly Leu Gly Leu
            100                 105                 110

Gly Tyr Arg Glu Thr Phe Arg Pro Ala Cys Asn Val His Asp Phe Gly
        115                 120                 125

Tyr Ala Asn Phe Pro Arg Phe Pro Ser Leu Tyr Asn Glu Thr Gly Arg
    130                 135                 140

Lys Leu Ser Asp Asp Asn Phe Leu Val Asn Met Asn Gln Ile Cys Arg
145                 150                 155                 160

Pro Arg Ser Phe Leu Ser Arg Ser Ala Cys Tyr Ser Ala Ala Tyr Ala
                165                 170                 175

Tyr Tyr Leu Ala Val Arg Ser Ala Gly Trp Ala Tyr Phe Tyr Asp
            180                 185                 190

<210> SEQ ID NO 3
<211> LENGTH: 140
<212> TYPE: PRT
<213> ORGANISM: Meiothermus silvanus

<400> SEQUENCE: 3

Met Arg Val Val Leu Leu Met Leu Val Leu Ala Ala Cys Gly
1               5                   10                  15

Ser Gln Thr Gly Ala Pro Asn Trp Thr Leu Glu Gln Ile Ala Ala Leu
            20                  25                  30

Thr Pro Glu Gln Ile Asp Ala Leu Ser Glu Gly Glu Leu Gln Lys Ile
        35                  40                  45

```
Gln Thr Ile Leu Gln Pro Glu Phe Ala Arg Val Glu Ser Gln Leu Ile
 50                  55                  60
Gln Leu Gln Ser Gln Leu Glu Ala Leu Val Ala Ala Gln Asp Ser Arg
 65                  70                  75                  80
Trp Pro Asn Phe Asp Tyr Thr Val Tyr Leu Ala Thr Ala Ile Pro Tyr
                 85                  90                  95
Gly Thr Phe Phe Thr Tyr Tyr Arg Thr Tyr Ser Gly Pro Asp Trp Ser
            100                 105                 110
Asn Asp Gly Cys Ser Tyr Ser Pro Asp Lys Pro Leu Phe Leu Asn Phe
        115                 120                 125
Lys Asp Pro Cys Asn His His Asp Phe Gly Tyr Arg
130                 135                 140
```

<210> SEQ ID NO 4
<211> LENGTH: 999
<212> TYPE: DNA
<213> ORGANISM: Chaetomium thermophilum

<400> SEQUENCE: 4

```
atgaagggct tcctgctggc cagcctggcc gccctggccg tggccgcccc cagcagcaag    60
aagcagcgcg ccgcccccgt gaccgcccag cagctgaaca acttcaagct gtacatgcag   120
tggagcagcg ccagccactg cgccaacgag gcccccatcg cagcgtggt gacctgcacc    180
gacaaccagt gcagcatgtt ccagagccac aacgccaccg tggccgccac cttcatcggc   240
agcatcctgg acatgcgcgg cttcctgggc atcgacgacg tggacaagaa catcgtgctg   300
agcttccgcg gcagcaccag ctggcgcaac tggatcgccg acgccatctt cgtgcagacc   360
ccctgcgacc tgaccccggg ctgcctggtg cacgccggct tctacgccag ctggctggag   420
atcaagaaca gcgtgatcga cgccgtgaag gccgccaagg ccgcccaccc caactacaag   480
ctggtgacca ccggccacag cctgggcgcc gccgtggcca cctggccgc cgccacccctg   540
cgcaaggccg gcatccccat cgagctgtac acctacggca gccccgcgt gggcaacaag    600
gccttcgccg agttcgtgac caaccaggcc ggcggcgagt accgcctgac ccacagcgcc   660
gaccccatcc ccgcctgcc ccccatcatc ttcaactacc gccacaccag ccccgagtac    720
tggttcgacg agggcgagga cggcgtggtg accgtgacg agttccagat ctgcgagggc    780
tacgccaacg tgaactgcaa cgccgccacc agcggcttca acatggacct gcacggctgg   840
tacttccaga ccaccagggg ctgcagcctg ggctacaccc cctggcgcgc cgtgaaggag   900
cgcgagctga cgaccccga gctggaggcc ctggtgaacc gcttcgccga tggacaag     960
gcctacgtgg agaacctgaa cctggagggc ctggagccc                          999
```

<210> SEQ ID NO 5
<211> LENGTH: 573
<212> TYPE: DNA
<213> ORGANISM: Meiothermus ruber

<400> SEQUENCE: 5

```
atgggcaagc ccatgcgctt cgccgtgggc atcctggccc tgctgctggc cgcctgcagc    60
cagcccgcca ccgagagcac cagcgccagc atcgtggagg acatgcgcca gctgggcgtg   120
gagcccgagg ccatcgccgc ctacaccgag gccctgcaga acctggagca ggcccgcctg   180
gccctgcaga gctgggcgc cggcgacctg ctgctggtgc agagcatcgc cctgggcagc   240
gtggccaact acgacgccta ctacaacgcc cgcgccagct accccagtt cgactggagc   300
cgcaacggct gcagcgcccc cgagggcctg ggcctgggct accgcgagac cttccgcccc   360
```

```
gcctgcaacg tgcacgactt cggctacgcc aacttccccc gcttccccag cctgtacaac        420
gagaccggcc gcaagctgag cgacgacaac ttcctggtga acatgaacca gatctgccgc        480
ccccgcagct tcctgagccg cagcgcctgc tacagcgccg cctacgccta ctacctggcc        540
gtgcgcagcg ccggctgggc ctacttctac gac                                     573

<210> SEQ ID NO 6
<211> LENGTH: 420
<212> TYPE: DNA
<213> ORGANISM: Meiothermus silvanus

<400> SEQUENCE: 6
atgcgcgtgg tgctgctgat gctggtgctg gtgctggccg cctgcggcag ccagaccggc         60
gcccccaact ggaccctgga gcagatcgcc gccctgaccc ccgagcagat cgacgccctg        120
agcgagggcg agctgcagaa gatccagacc atcctgcagc ccgagttcgc ccgcgtggag        180
agccagctga tccagctgca gagccagctg gaggccctgg tggccgccca ggacagccgc        240
tggcccaact tcgactacac cgtgtacctg gccaccgcca tccctacgg caccttcttc        300 acctactacc gcacctacag cggcccccgac tggagcaacg acggctgcag ctacagcccc        360
gacaagcccc tgttcctgaa cttcaaggac ccctgcaacc accacgactt cggctaccgc        420
```